(12) United States Patent
Spigelman et al.

(10) Patent No.: US 6,731,966 B1
(45) Date of Patent: May 4, 2004

(54) SYSTEMS AND METHODS FOR TARGETING A LESION

(76) Inventors: Zachary S. Spigelman, 88 Claremont St., Newton, MA (US) 02458; Richard H. Theriault, 5 Brooks Hill Rd., Lincoln, MA (US) 01773

(*) Notice: Subject to any disclaimer, the term of this patent is extended or adjusted under 35 U.S.C. 154(b) by 0 days.

(21) Appl. No.: 09/565,183

(22) Filed: May 3, 2000

(65) Prior Publication Data (65)

Related U.S. Application Data

(63) Continuation-in-part of application No. 08/880,477, filed on Jun. 23, 1997, now Pat. No. 6,119,033.
(60) Provisional application No. 60/132,296, filed on May 3, 1999, and provisional application No. 60/039,285, filed on Mar. 4, 1997.

(51) Int. Cl.[7] .................................................. A61B 5/05
(52) U.S. Cl. ...................... 600/407; 600/410; 600/417; 600/461; 378/37
(58) Field of Search ............................ 600/407, 410, 600/461, 567, 417; 378/37, 417

(56) References Cited

U.S. PATENT DOCUMENTS

| 5,042,486 A | | 8/1991 | Pfeiler et al. | ............... 128/653 |
| 5,211,165 A | * | 5/1993 | Dumoulin et al. | ........... 128/899 |
| 5,279,309 A | | 1/1994 | Taylor et al. | ............... 128/782 |
| 5,377,678 A | | 1/1995 | DuMoulin et al. | .......... 128/653 |
| 5,386,447 A | | 1/1995 | Siczek | .......................... 378/37 |
| 5,415,169 A | * | 5/1995 | Siczek et al. | ............... 600/427 |
| 5,577,502 A | | 11/1996 | Darrow | ........................ 128/653 |
| 5,647,373 A | | 7/1997 | Paltieli | ........................ 128/749 |
| 5,776,062 A | | 7/1998 | Nields | ........................ 600/407 |
| 5,787,886 A | * | 8/1998 | Kelly et al. | .................. 600/407 |
| 5,868,673 A | * | 2/1999 | Vesely | .......................... 600/407 |
| 6,102,866 A | * | 8/2000 | Nields et al. | ................ 128/915 |
| 6,459,925 B1 | * | 10/2002 | Nields et al. | ................ 600/427 |

FOREIGN PATENT DOCUMENTS

| DE | 39 02 249 A1 | 2/1990 | |
| DE | 42 25 112 C1 | 9/1993 | |
| DE | 44 18 868 A1 | 11/1995 | |
| EP | 0 600 610 A2 | 8/1994 | |
| FR | 2 719 760 | 11/1995 | |
| WO | WO 93/14712 | 5/1993 | |
| WO | WO 94/23647 | 10/1994 | |
| WO | WO 96/11624 | 4/1996 | ................. 600/426 |
| WO | WO 97/03609 | 2/1997 | |
| WO | WO 97/29682 | 8/1997 | |

OTHER PUBLICATIONS

International Search Report completed on Sep. 4, 2000 and mailed on Oct. 4, 2000.

\* cited by examiner

*Primary Examiner*—George Manuel
*Assistant Examiner*—Barry Pass
(74) *Attorney, Agent, or Firm*—Foley Hoag LLP

(57) ABSTRACT

The present invention provides systems and methods for guiding a surgical instrument into a preselected spatial relationship with a lesion, in particular a lesion of the breast. In an exemplary embodiment, the system includes a data translation system that translates a set of data points representing the position of the lesion into a set of three dimensional coordinates, and also includes a tracking system that tracks the position of a surgical instrument in three dimensional space, and further includes a representation system that produces a representation of the position of the surgical instrument relative to the lesion. The systems of the present invention are correlated with methods for biopsying a lesion and for surgically removing a lesion.

22 Claims, 7 Drawing Sheets

SYSTEMS AND METHODS FOR TARGETING A LESION

CROSS-REFERENCE TO RELATED APPLICATIONS

This application is a continuation-in-part of U.S. Ser. No. 08/880,477, filed Jun. 23, 1997, now U.S. Pat. No. 6,119,033 which claims the benefit of U.S. Provisional Patent Application Ser. No. 60/039,285, filed Mar. 4, 1997, and this application further claims the benefit of U.S. Provisional Patent Application Ser. No. 60/132,296, filed May 3, 1999, the contents of which are incorporated by reference.

FIELD OF THE INVENTION

The present invention relates generally to systems and methods for directing a surgical instrument into a position relative to a tissue area whose position has been preselected. More specifically, the present invention relates to systems and methods adapted for directing a surgical instrument into a position relative to a lesion in the breast.

BACKGROUND

Techniques and devices available in the prior art for directing surgical instruments towards areas of breast tissue fall into two categories: those applicable to palpable lesions and those applicable to non-palpable lesions. Commonly, the use of these systems and methods result in a section of tissue being removed so that its gross and microscopic anatomy can be examined.

Palpable lesions are accessible by techniques commonly available in the medical arts, including the use of percutaneous techniques and the use of open surgical techniques. Percutaneous techniques involve the use of a medical device to reach a tissue area located beneath the skin surface without incising the tissues to approach the tissue area directly. Percutaneous techniques in surgery can include the formation of a skin incision through the epidermis and the dermis for the purpose of facilitating the introduction of the medical device through the skin, though the remainder of the delivery of the device to the tissue area takes place without further incisional exposure. Percutaneous techniques as applied to the breast include core needle biopsy and fine needle aspiration biopsy. Open surgical techniques are understood to involve the use of surgical methods to approach the tissue area directly. Surgical methods include incising the skin, and further include carrying the approach beneath the skin level to the area of tissue to be removed. Surgical methods include dissection, either sharp or dull, through an area of tissue. When a tissue area is palpable, the operator identifies the pertinent tissue area by palpation and uses this identification to guide the medical instrument to the desired area relative to the palpable tissue area.

When a tissue area is not palpable, other methods must be employed to identify its location and guide the medical instrument thereto. In the breast, non-palpable tissue areas can be identified through mammography and ultrasound. Other modalities available in the medical arts for the identification of tissue areas include CT scan and MRI, each with applicabilities well known in the medical arts. With reference to the breast, mammography is commonly employed to diagnose tissue areas that may contain possible foci of pathological changes that are cancerous or precancerous. Mammography permits the recognition of pathological tissue areas before they develop into palpable masses that may indicate more advanced cancers. When an abnormal area is identified by mammography, further diagnosis may be required. Such diagnosis may include a biopsy.

Systems and methods for biopsy of abnormalities identified on mammography are well known in the medical arts. A biopsy may be performed percutaneously or through an open surgical procedure. Either type of biopsy typically includes a way to localize the tissue area to be targeted with the biopsy device. As used herein, a tissue area of concern for a biopsy is termed a lesion. A palpable lesion can be localized by palpation. A non-palpable lesion that has been identified by mammography may be approached percutaneously for biopsy using mammography methods for guidance. If a percutaneous technique is used, the breast can be held in an apparatus that compresses it and that permits its radiological examination as a biopsy needle is directed towards the lesion. Mathematical methods to determine the location of the tissue area within the compressed breast allow more precision in directing the needle to the tissue area.

However, certain technical difficulties are understood to accompany the use of mammography systems to approach tissue areas for biopsy. For example, compression introduces certain artifacts and makes the position of the tissue area more difficult to locate precisely; this is a particular problem for lateral portions of tissue. Furthermore, multiple mammograms and multiple biopsies may need to be performed to give assurance that representative tissue sections have been obtained to diagnose the condition on the tissue area initially perceived on the screening mammogram. Although mechanized systems have been devised to automate the biopsy-taking process by taking multiple specimens or by taking a large specimen volume, the need for multiple mammograms and multiple biopsies often remains.

Surgical biopsies of non-palpable lesions must be also guided so that they reach the tissue area of concern. Commonly this takes place by a preliminary procedure such as a needle localization in which a needle tip is placed by the radiologist in the tissue area that has been identified mammographically. Typically, when a biopsy is guided by needle localization, the patient is taken to the mammography suite before the surgical biopsy for the placement of a guiding needle. As a first step, the patient is placed in a mammography machine, with her breast in mammographic compression. An upper compression plate containing an opening with a superimposed localizing grid is centered over the breast lesion. A mammography is performed in two perpendicular directions with the suspicious lesion placed in the opening of the grid. A radiologist then uses the grid seen on the mammograms to guide the placement of the prelocalization needle. A prelocalization needle is directed to the tissue area. The position of the needle is verified relative to the area requiring biopsy. Multiple needle positionings and mammographic confirmations may be required. When the appropriate position has been attained, a small wire with a hook at its end, called a wire, is placed through the bore of the needle so that its tip rests in the area requiring a biopsy. The needle is removed and the wire remains in place. The wire is secured so it will not become dislodged. The patient is transferred to the surgical suite, where she is prepared for the surgical biopsy. The surgeon uses the wire as a guide towards the area requiring biopsy. When the surgical biopsy is performed, a tissue sample is taken, corresponding with the amount of suspicious tissue seen on mammogram surrounding the needle tip. This excised tissue sample is mammogrammed after excision, and the film obtained from the specimen is compared with the original mammogram to confirm that the tissue area identified on the original mammogram has been adequately excised.

A surgical biopsy can be performed to remove a segment of tissue from a larger tissue mass that is abnormal-looking on mammography. The segment of tissue can then yield a diagnosis that then guides further therapy. Alternatively, if an abnormal-looking area has already been diagnosed, a surgical procedure can be performed that excises the entire abnormal area for definitive therapy. This procedure is termed a wide excision, because the abnormal area is excised widely, that is with a rim of normal tissue around it. As understood herein, the term biopsy can be applied to a wide surgical excision. Wide surgical excisions are currently commonly performed using needle localization techniques as described above, so the surgeon can identify the area within the breast to be excised. The term wide surgical excision, as used herein, includes what is commonly termed a lumpectomy.

Needle localization techniques have limitations. First, multiple positioning attempts and mammographic confirmations may be required. Second, when used as a preliminary procedure, the patient must usually be transported from the mammography suite to the operating suite, potentially increasing patient stress, time delay and procedure cost. Further, the surgical procedure cannot be carried out until the localization is complete, so if there is difficulty placing the localization wire, the surgical team and operating room remain in a state of readiness, wasting time and personnel resources. Third, there are inaccuracies that affect the accuracy of the J-wire in guiding the surgeon. For example, the wire may become dislodged, or its tip may not accurately reflect the best tissue area to be removed. Or, for example, there may be a shift of the J-wire with respect to the tissue area as the breast moves from the compressed to the non-compressed state. As another example, following the J-wire into the lesion may be technically difficult. As a further example, combining the J-wire position with the two-dimensional mammography images may not tell the surgeon enough about the three-dimensional shape of the lesion so that the surgeon can remove the lesion completely along with a rim of normal tissue around it. Because of the variety of inaccuracies that afflict needle localization guided biopsies, multiple surgical biopsies may be required to sufficiently remove the tissue area of concern. Multiple surgical biopsies may require additional surgical procedures, adding further to the patient's suffering and anxiety, and multiplying medical costs.

It is desirable therefore to provide systems and methods that will yield accurate diagnosis of breast lesions without incurring the risks of imprecise needle localization. It is further desirable that a technique for biopsy be provided that is efficient, cost-effective and minimally stressful to the patient. It is also desirable that systems and methods be provided that facilitate the physician's access to the lesion, for purposes of biopsy or extirpation.

SUMMARY OF THE INVENTION

In one embodiment, the present invention includes systems for placing a surgical instrument into a spatial relationship with a lesion. The system may include a data translation system that translates a set of data points that identify the lesion in at least two two-dimensional planes into a set of three-dimensional coordinates that identify the position of the lesion in three-dimensional space. The system may also include a tracking system that is related to the surgical instrument that generates tracking signals for identifying the position of the surgical instrument in three-dimensional space. The system may also include a representation system that produces a representation of the positions of the surgical instrument and the lesion in three-dimensional space relative to each other, based on the signals generated by the tracking system and the set of three-dimensional coordinates produced by the data translation system, wherein the placement of the surgical instrument into spatial relationship with the lesion is guided by reference to the aforesaid representation.

In one embodiment, the present invention includes a system for guiding the placement of a surgical instrument into spatial relationship with a lesion including a data translation system, a positioning system, a tracking system and a representation system. In this embodiment, the data translation system may translate a set of data points identifying the lesion in at least two two-dimensional planes into a set of three-dimensional coordinates that identify the lesion in three-dimensional space. In this embodiment, the positioning system may identify the position of the lesion in three-dimensional space relative to a three-dimensional position of at least one anatomic landmark. In this embodiment, the tracking system may be disposed in relation to the surgical instrument to generate tracking signals identifying the position of the surgical instrument in three dimensional space. In this embodiment, the representation system may produce at least one representation of the position of the surgical instrument in three-dimensional space related to the position of the lesion or the spatial landmark, so that the placement of the surgical instrument into spatial relationship with the lesion is guided by reference to the representation.

In one embodiment, the invention includes a mammography system for orienting a breast to facilitate the biopsy of a breast lesion. In this embodiment, the mammography system includes a mammography device that may obtain mammograms in at least two different planes and that may obtain mammograms in a plurality of planes relative to a defined axis of the breast, a first set of mammograms that identify the position of the lesion within the breast, a first set of two-dimensional coordinates corresponding to the first set of mammograms, an adjustment system that generates a set of positional instructions that direct the positioning of the mammography device relative to the breast for obtaining a second set of mammograms that show the lesion centrally located on at least one film, and a compression system for securing the breast so that the position of the lesion within the breast corresponds to the position of the lesion located on the second set of mammograms.

In another embodiment, the invention includes a method for obtaining a tissue sample from the breast. This practice of the invention includes identifying the position of the target tissue on at least two mammograms, digitizing data correlated with the mammograms, determining the position of the target tissue in three dimensional space using the digitized data, providing a surgical instrument suitable for obtaining a sample of the target tissue, electronically tracking the position of the surgical instrument relative to the target tissue, creating a two-dimensional representation of the position of the surgical instrument, directing the surgical instrument to the target tissue by referring to the two-dimensional representation, and using the instrument to obtain a sample of the target tissue.

BRIEF DESCRIPTION OF THE DRAWINGS

FIGS. 6 and 6A show a schematic perspective view of an operator identifying anatomic landmarks in a free-form breast in a sterile setting.

DETAILED DESCRIPTION

Figures 1, 1A:
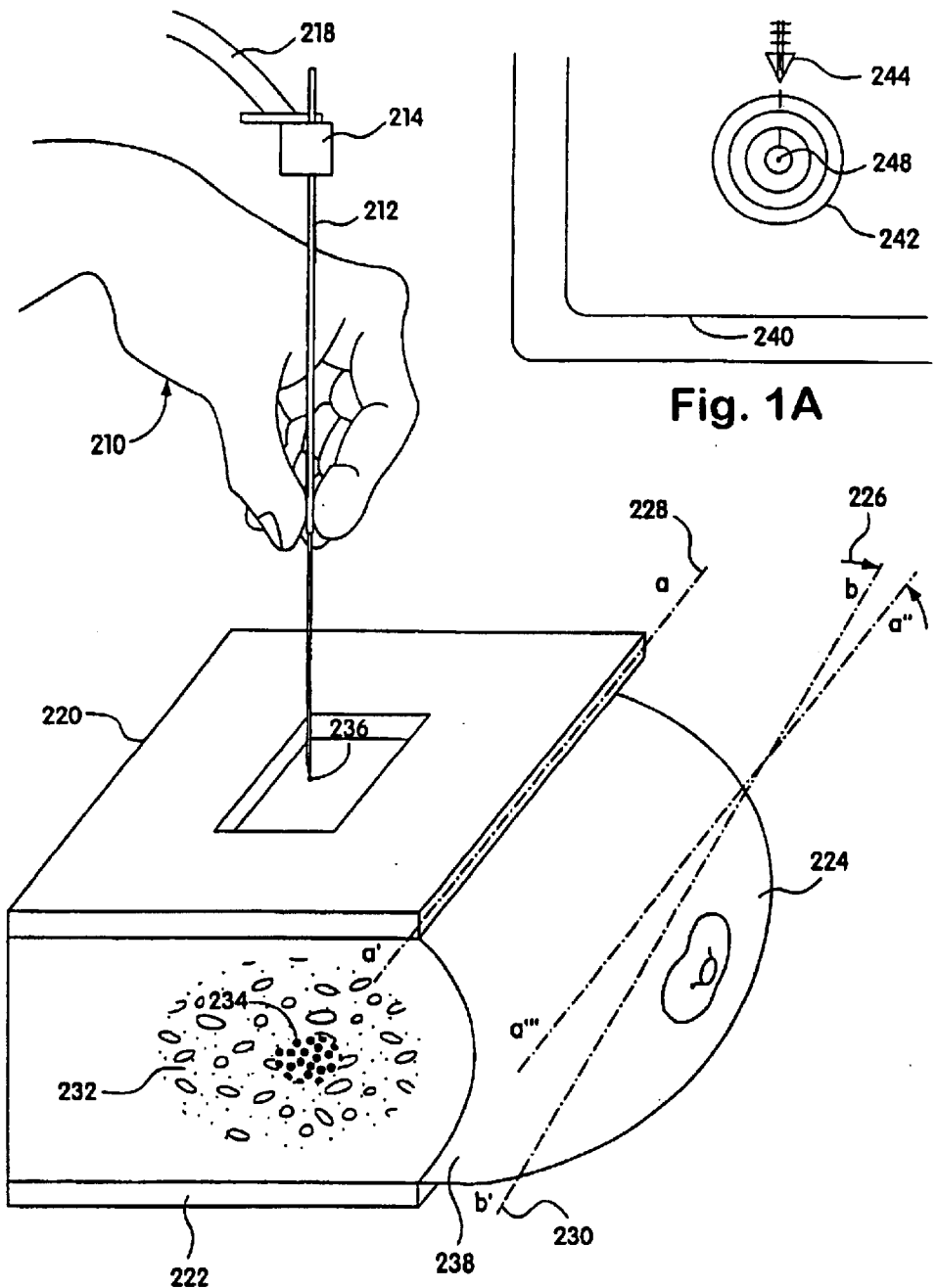
FIGS. 1 and 1A show a schematic perspective view of an operator directing a surgical instrument towards an identified lesion in a breast in accordance with the systems and methods of the present invention.

The present invention provides improvements in the targeting of tissue areas for biopsies and related procedures. As an illustrative embodiment, the systems and methods of the present invention will be applied to the targeting of tissue areas within the breast.

Definitions:

As understood herein, the term biopsy includes the removal of a body tissue of any size or amount that includes the examination of its gross or microscopic; biopsies can be directed, for example, towards grossly identifiable tissues, microscopic tissues not visible to the naked eye, or individual cells that may be suspended in a body fluid. As used herein, therefore, the term biopsy would include those surgical procedures where tissues are removed for definitive therapy of an abnormality insofar as those procedures result in the removal of a body tissue that is grossly and/or microscopically examined. As used herein, the term biopsy further includes those diagnostic modalities involving contact with a tissue area to determine tissue abnormalities by employing techniques permitting tissue evaluation without tissue removal. As examples, this type of biopsy can include the optical evaluation of the tissues, for example by fluorescence, the thermal evaluation of the tissue, electromagnetic evaluation of the tissue, the chemical evaluation of the tissue, the biochemical evaluation of the tissue or the immunological evaluation of the tissue. This type of biopsy technique includes, without restriction, diagnostic modalities developed through the genetic or biotechnology arts that can be adapted for the local diagnosis of in vivo tissue abnormalities.

As understood herein, a surgical instrument can include any tool adapted for performing a biopsy. A surgical instrument, as understood herein, can include any device adapted for positioning a diagnostic modality into contact with or biological juxtaposition to an in vivo tissue to evaluate an abnormality of said tissue. Examples of surgical instruments can include excisional devices such as needles or scalpels, as well as probes, catheters or other tools that can bear a biopsy device to a specified tissue area. A surgical instrument further can include any tool adapted for treating or extirpating a lesion, including those tools or systems that can direct a therapeutic modality into proximity with a lesion. A therapeutic modality may include any intervention that treats a pathological process. As an example, a therapeutic modality may include chemotherapy or other drug therapy, phototherapy, radiotherapy or the application of electromagnetic energy to treat a pathological process. Hence, a surgical instrument may refer to any tool adapted for directly or indirectly directing a therapeutic modality towards an area of pathology. A surgical tool may directly impart therapy, as in a tool that provides for delivery of heat energy or other electromagnetic energy to an area of pathology. A surgical tool may indirectly direct a therapeutic modality, for example, by positioning a drug delivery system, a radiotherapeutic implant or a source of electromagnetic energy in proximity to an area of pathology. Other types of surgical tools that directly or indirectly treat pathological processes will be readily envisioned by those of ordinary skill in the art.

As understood herein, a spatial relationship with a lesion includes any position preselected by the operator as the desired location of the surgical instrument with respect to the lesion. For example, such a spatial relationship can include the placement of a surgical tool at a preselected distance from the lesion so that the surgical tool can perform a wide excision thereof with a preselected amount of normal tissue surrounding the lesion. As another example, a spatial relationship with a lesion can include placing a biopsy device in certain preselected positions with reference to the lesion so as to evaluate the health of the tissues in those locations.

As understood herein, a data translation system may include any device that translates a set of data points identifying the position of the lesion in at least two two-dimensional planes into a set of three-dimensional co-ordinates, wherein said set of three-dimensional coordinates identifies the position of the lesion in three- dimensional space. Software can be provided to effect this translation. The set of data points can be obtained from any source. These data points, for example, can be obtained from a prior or a concurrent digital mammogram. These data points, as another example, can be obtained by digitizing a set of film mammograms. These data points can be obtained from any other system capable of evaluating the position of the lesion, such systems not being limited to mammography. For example, the data points can be obtained from ultrasonography of a breast, from MRI, from thermography or from any other system adapted for providing such information. Data points can also be derived from other modalities as appropriate for specific tissue areas. Conventional X-ray modalities, as understood by practitioners in the art, may be employed, as may radionuclide scans, CT scans or any other scan adapted for providing positional data.

As understood herein, a tracking system includes any device that is adapted for identifying the position of the surgical instrument being placed in spatial relationship to the lesion. According to these systems and methods, a tracking system may be disposed in a selected relation to the surgical instrument, generating tracking signals for identifying the position of the surgical instrument in three-dimensional space. Although in one embodiment of these systems, the tracking system includes a sensor affixed to the proximal end of the surgical instrument that permits tracking of the distal tip of the instrument, any other positional relationship can be constructed without departing with the scope of the invention disclosed herein. For example, a tracking system can include a positional probe affixed to the distal tip, or a sensor system surrounding the surgical instrument that relays signals regarding the three-dimensional position of the surgical instrument. Other arrangements of a tracking system can be envisioned by those of ordinary skill in these arts without departing from the scope of the systems and methods of the present invention.

As understood herein, a representation system according to these systems and methods may include any system that produces a representation of the position of the surgical instrument and the position of lesion in three-dimensional space relative to each other. Software can be provided to effect this representation. This representation can take any form that conveys the desired information. For example, a three-dimensional holographic simulation can be formed. Alternatively, a set of two-dimensional images can be formed. A single two-dimensional image can be formed that uses additional indicia of three-dimensional relationality. Such indicia can include brightness, intensity, color, sound or any other indicia that can be devised by skilled artisans in this field. A representation can convey information in a graphical or non-graphical form. A representation can convey information as a set of data points to be received by a device adapted for the reception or processing of such data points. Since a plurality of representational forms can be envisioned by those of skill in the relevant arts, the scope of the claims below are not to be restricted to the specific embodiments disclosed herein.

As understood herein, an anatomic landmark may include any anatomic feature of the body. An anatomic landmark may be identified as a feature existing within another anatomic structure. An anatomic landmark can include an area of skin or bone. Further, an anatomic landmark can include a structure within the body such as a lymph node, a duct, a blood vessel or a cyst. The anatomic landmark provides a landmark relative to which the positioning system can identify the position of the lesion. The anatomic landmark may be securely fixed in a particular position, like a bone. An anatomic landmark may be capable of mobility, like a cyst or a duct. The positioning system disclosed herein is capable of determining the three dimensional position of the anatomic landmark at a particular point in time and correlating the position of the lesion thereto. An example of a technology that can identify anatomic landmarks is ultrasound. Other technologies, appreciated by practitioners in these arts, are available to provide a three-dimensional position of an anatomic landmark so that the positioning system can identify the position of the lesion relative thereto.

As understood herein, an introduction system may include any system for directing the surgical instrument in a selected direction relative to the selected tissue area. An introduction system can include either human or non-human agents to direct the surgical instrument. A machine or a robotic mechanism can direct the surgical instrument. Alternatively, a human operator can direct the surgical instrument, or can direct the machine inserting the surgical instrument.

As understood herein, the term mammography system refers any mammography system familiar to practitioners of ordinary skill in the art. In an embodiment of particular utility, however, the mammography system, as the term is used in the present invention, comprises the features of the mammography system further disclosed as part of these systems and methods. Such a mammography system, in one embodiment, includes a mammography device for obtaining mammograms in at least two different planes and capable of obtaining mammograms in a plurality of planes relative to a defined axis of a breast, a first set of mammograms, wherein said first set of mammograms identifies a position of the breast lesion within the breast, a first set of two-dimensional coordinates that corresponds to the first set of mammograms, an adjustment system that generates a set of positional instructions for the mammography device, wherein the set of positional instructions directs the positioning of the mammography device relative to the breast to obtain a second set of mammograms wherein the breast lesion is located centrally on at least one mammogram, and a compression system for securing the breast in relation to the mammography system so that the position of the lesion within the breast relative to the mammography system corresponds to the position of the lesion located on the second set of mammograms, thereby orienting the breast to facilitate the biopsy of the breast lesion. The mammography system as disclosed in the present invention is advantageously combined with the other features of a system for obtaining a tissue sample from a selected area of the breast.

In one embodiment, the mammography system of the present invention can direct a mammography device for reorientation so that the target lesion is located in the center of a mammographic field. When compressed in that position, the lesion is amenable for biopsy. Lesions located in the center of a mammographic field can be easier to biopsy than lesions more peripherally located. The systems and methods of the present invention permit biopsies to be taken from a plurality of approaches relative to the lesion. In one embodiment, after the mammography device has been repositioned so that the lesion is located in the center of mammographic field, the mammography system as described herein is interfaced with the other components of a system for obtaining a tissue sample from a selected area of the breast. In this embodiment, a tracking system is available for tracking the three dimensional position of a surgical instrument relative to the selected areas of the breast. In one embodiment, the position of the surgical instrument relative to the lesion can be identified in part by touching the tip of the surgical instrument to the skin at the location where the needle is to be inserted into the skin. The positional representation system adjusts for the needle position relative to the lesion and creates a representation to guide the needle to the lesion even if the angle of needle insertion is varied from 90 degrees, and even if the direction of needle insertion relative to the breast is an atypical one. Further, the mammography system may be adapted for permitting biopsies to be taken from a plurality of angles.

Description of Illustrated Embodiments:

FIGS. 1 and 1A show a representative embodiment of the systems and methods of the present invention. As shown in FIG. 1, a surgical instrument 212 may be inserted into a patient's breast 224 by an operator 210 in order to biopsy a lesion 234. The lesion 234 is shown in FIG. 1 in a partial cut-away view of the breast 224, where the skin is schematically excised along the line 238, to reveal schematically the breast parenchyma 232 with the lesion 234 buried therein. A surgical instrument 212 may include any surgical instrument, as discussed above, In a representative embodiment, the surgical instrument 212 may be a pre-localization needle that can be used to place a facilitate the placement of a J-wire or comparable device for needle localization. In the depicted embodiment, the surgical instrument 212 bears at its distal end a needle holder assembly 214 that contains a position sensor (not shown) integrated with a tracking system (not shown) that tracks the position of the surgical instrument 212, here a needle. The sensor on the needle holder assembly 214 is in electrical communication through a cable 218 that carries signals to the tracking system, described in more detail below. In the depicted embodiment, the surgical instrument 212 is being directed towards a breast lesion 234 by the operator 210 who is able to view a representational image 242 on a user interface 240. The patient's breast 224 in the illustrated embodiment is compressed between an upper compression plate 220 and a lower compression plate 222. These plates have been applied to the breast along a selected plane 228 shown as a–a' that has been selected so that craniocaudad mammographic x-rays as shown here, would be delivered at right angles to the lesion. The method by which the selected plane 228 may be selected will be desribed in more detail below. With the breast held in this position between the compression plates 220 and 222, the surgical instrument 212 can be inserted into the lesion 234 through a cutaneous insertion point 236 at an angle perpendicular to the selected plane 228. Data from screening mammograms can be used to ascertain the selected plane 228 at which to orient the mammography apparatus for taking lateral and craniocaudad diagnostic mammograms. The angle by which the mammography apparatus is adjusted is represented at 226 as the angle between the craniocaudal angle plane 230 shown at b–b' and the selected plane 228 a–a' or the plane shown at a"–a'" which is parallel to the selected plane 228.

The systems and methods of the embodiment depicted in FIG. 1 and 1A can use two dimensional mammographic views to obtain a three dimensional position of the lesion within the patients breast, further providing mathematical corrections to compensate for the movement of the lesion due to mammographic compression, as well as to adjust for the parallax error introduced by the radial splaying of x-rays away from the vertical line. An example of these methods is provided below as Example 1.

The systems and methods of the depicted embodiment further can provide three-dimensional information about the location of a surgical instrument 212. FIG. 1A shows displayed on a user interface 240 an image 242 of the relationship between the surgical instrument 212 and the lesion 234. The image 242 depicted here includes a non-representational image 244 of the position of the surgical instrument and a non-representational image 248 of the position of the lesion. The depicted embodiment provides a visual image that depicts the relationship of the image to the lesion as a two-dimensional image. Alternatively, a visual image may be created that represents three-dimensionally the relationship of the instrument to the lesion, or it can produce a two dimensional image that simulates three dimensionality. The representation system can depict a changing relationship of these structures in three-dimensional space, where the changing is depicted in real time.

The visual image produced can furthermore be representational or non-representational, where the term "representational" is understood to mean that the image attempts to display with pictorial accuracy the components it represents. The visual image 242 shown in FIG. 1A is a non-representational in that it presents symbols that stand for the relationship between the imaged components. Combinations of representational and nonrepresentational images can also be used together as part of a single or a plurality of visual images. A representational image of a needle approaching the lesion, for example, would look like a needle as it approached an image that looked in some way "like" the breast lesion. By contrast, a non-representational visual image is understood to comprise the universe of abstractions in which a symbol or a set of symbols are used to convey the desired information about the proximity of the surgical instrument to the lesion. For example, a symbol can be chosen to represent the needle, the lesion and their proximity In the embodiment illustrated in FIG. 1A, the target symbol can symbolize proximity between the position of the surgical instrument and the position of the lesion, with the surgical instrument's position being shown as an image 244 moving relative to the image symbolizing the lesion 248. As another example, horizontal and vertical lines can be drawn intersecting at their midpoints, with the surgical instrument's position showing up as a point on the screen being directed towards the point of intersection of the lines, Such a set of symbols may indicate the position of the needle relative to the lesion in the craniocaudal and the mediolateral planes, while an additional symbol may be employed to demarcate the position of the needle in the anterior-posterior plane. For example, color changes can indicate anterior-posterior proximity to the lesion, or an additional graphic symbol, for example a thermometer symbol, can show the needle's closeness in this plane. Since other types of visual images, both representational and nonrepresentational, may be envisioned by those of ordinary skill in the arts, the examples provided above should not be viewed as limiting the scope of the claims for these systems and methods.

In one embodiment, the visual representation can be an abstract one. It can be a single integrated view that provides information regarding the plane of the lesion as well as its depth. When the proximal end of the needle and its distal tip are in the same plane as the lesion, the representation can be of a circle with a crosshair inside it. When the two are not in the same plane, the circle can be distinct from the crosshair, allowing the user to line up the needle precisely with the lesion before even penetrating the breast. As the needle approaches the lesion, there can be a representation of concentric circles with the lesion at the center; according to this embodiment, the user must keep the circle and the crosshair aligned at all times while entering the breast and proceeding to the lesion. Furthermore, in an embodiment there can be a representation of the distance from the lesion with the scale in centimeters when the distance from the lesion is high and dropping down to millimeters when the needle gets closer to the lesion. The lesion can appear magnified as it is approached. There can be a virtual dotted line from the tip of the needle to the lesion that may provide a path that the radiologist can follow to reach the lesion. The color of the circle and crosshair can change when the needle has reached the center of the lesion.

An example of methods for providing an image according to the present invention is presented in Example 1.

Figure 2:
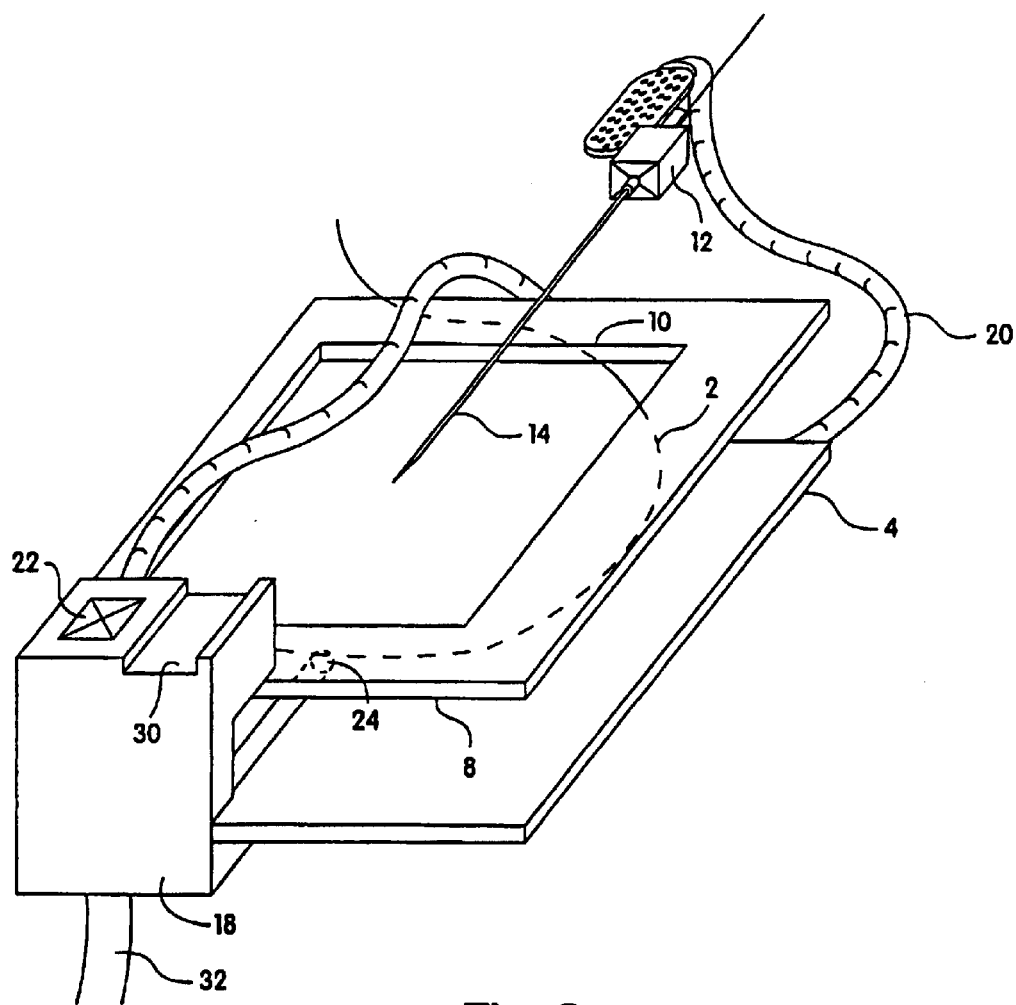
FIG. 2 shows a perspective view of an embodiment of a lesion tracking system applied to a patient.

FIG. 2 shows in more detail an embodiment of the present invention as applied to a patient's breast 2. In this figure, the patient's breast 2 (shown in dotted lines) is compressed in a mammography system between an upper mammogram plate 8 and a lower mammogram plate 4. The breast 2 is shown to be compressed craniocaudally to prepare it for the insertion of a surgical instrument, here a needle 14. The needle 14 is affixed to a detachable needle holder assembly 12 at its distal end. Included in the needle holder assembly 12 is a position sensor (not shown) that gathers signals related to the position of the needle. The position sensor is integrated with the tracking system of the present invention, as described herein. The position sensor is in electrical communication through a cable 20 with the fixed part 18 of the tracking system, shown here as related to the upper mammogram plate 8 and lower mammogram plate 4. In one embodiment, the fixed part 18 of the tracking system may be adjusted so that it can be affixed to both mammogram plates after the breast has been compressed between them. Other affixations also may be suitable, so that the fixed part 18 remains in a stable stationary relationship to the mammogram plates or to the compressed breast during the biopsy procedure. In the depicted embodiment, a radio-opaque reference marker 24 is shown situated on the lower mammogram plate 4 to aid in the calibration and orientation of the tracking system. As depicted in FIG. 2, the fixed part 18 of the tracking system is located at the lateral aspect of the mammogram plates, so that in this figure the fixed part 18 is situated lateral to the lateral aspect of the patient's compressed right breast. This arrangement is for convenience only, and other arrangements may be set up to position the fixed part 18 that accommodate the needs of the operator. A calibration cross 22 is integrated with the fixed part 18 of the tracking system to allow its calibration, as described in the present application. The fixed part 18 of the tracking system also bears a platform 30 for holding the needle holder assembly 12 when it is not in active use directing a surgical instrument. A cable 32 or set of cables may connect the fixed part 18 of the tracking system with the other components of the guidance system. In other embodiments, a transmitter may be attached to the fixed part 18 to transmit signals to the other components of the system. There is an access window 10 adapted for positioning over a lesion of the breast 2 so that the needle 14 can penetrate the lesion at a direct angle through the window 10. The access window 10 is dimensionally adapted for permitting access to a breast lesion for biopsy while still maintaining compression of the breast in a preselected position. In certain embodiments, the access window 10 may comprise a grid or a screen, or may contain a plurality of removable segments, or may comprise multiple insertion pores. In certain embodiments, the access window 10 may be fabricated partially or entirely from a structurally stable material that is readily penetrable by the needle 14. The access window 10 may be adapted for use on a single patient and may be disposable. Other configurations of the access window 10 may be known or devised with no more than routine experimentation by ordinary skilled practitioners.

Figure 3A:
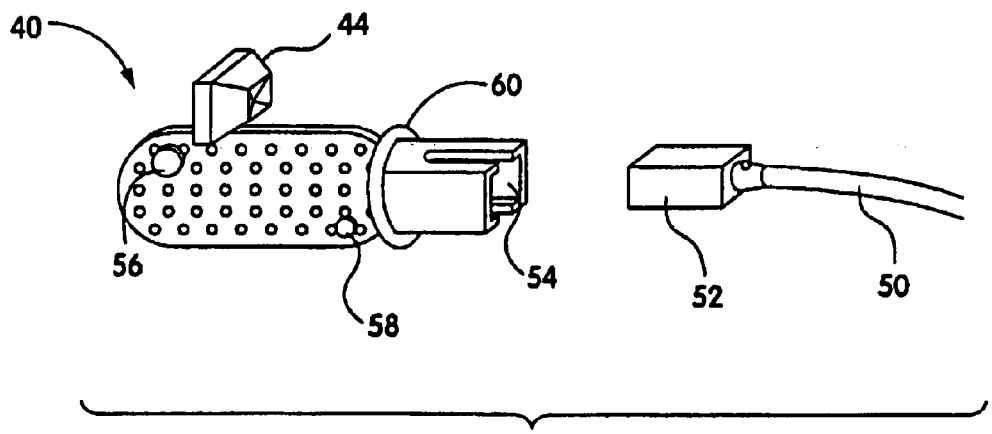
FIGS. 3A–C show embodiments of components of a needle holder assembly.
Figure 3B:
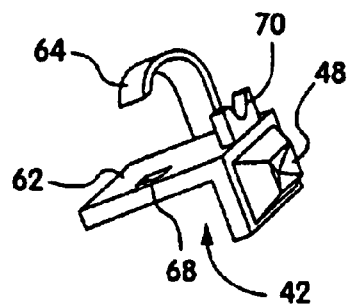
Figure 3C:
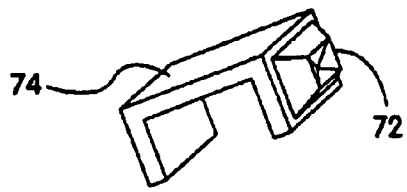

FIGS. 3a, 3b and 3c show in more detail features of the system depicted in FIG. 2. FIG. 3a shows a perspective view generally of a needle holder assembly 40 adapted for attachment to a needle using a saddle assembly 42 depicted generally in FIG. 3b. The needle holder assembly 40 is attached to the saddle assembly 42 through a coupler 44. The attachment of the needle holder assembly 40 to the saddle assembly 42 is released through a disengagement mechanism 56. The disengagement mechanism 56 is adapted for releasing the connection between the needle holder assembly 40 and the saddle assembly 42 so as to avoid transmitting force to the saddle assembly that might dislodge or move the needle after it is positioned. A tracking sensor (not shown) can be included as part of the saddle assembly 42 or as part of the needle holder assembly 40. Signals from the tracking sensor are conveyed to the other components of the tracking system through a cable 50. The cable terminates in a male plug end 52 that can be inserted in a female socket 54. An ejector mechanism 58, for example a mini-Bird ejector, triggers the release of the male plug end 52 from the female socket 54 in such a way as to minimize any force being transmitted through the needle holder assembly 40 to the needle (not shown). A protective sheath 60 can be deployed over the plug end 52 within the socket 54 to cover the cable 50 and ensure its sterility. By reference to FIG. 3b, further features of this embodiment can be appreciated. FIG. 3b shows generally perspective view of a saddle assembly 42 adapted for attachment to a biopsy needle, a prelocalization needle for needle localization or any surgical instrument (not shown). In this figure, a platform 62 can be seen providing a stable base for a needle hub or another similarly shaped surgical instrument. A belt 64 is available to affix the needle firmly to the platform 62. The belt 64 is locked by insertion into a locking slot 68. A cradle 70 is shown adapted to hold the proximal end of the needle hub. The saddle assembly 42 is connected with the needle holder assembly 40 of FIG. 3a by way of a coupling end 48. FIG. 3c shows a perspective view of a calibration device 72 incorporated into a bed 74 for the needle holder assembly.

Figure 4:
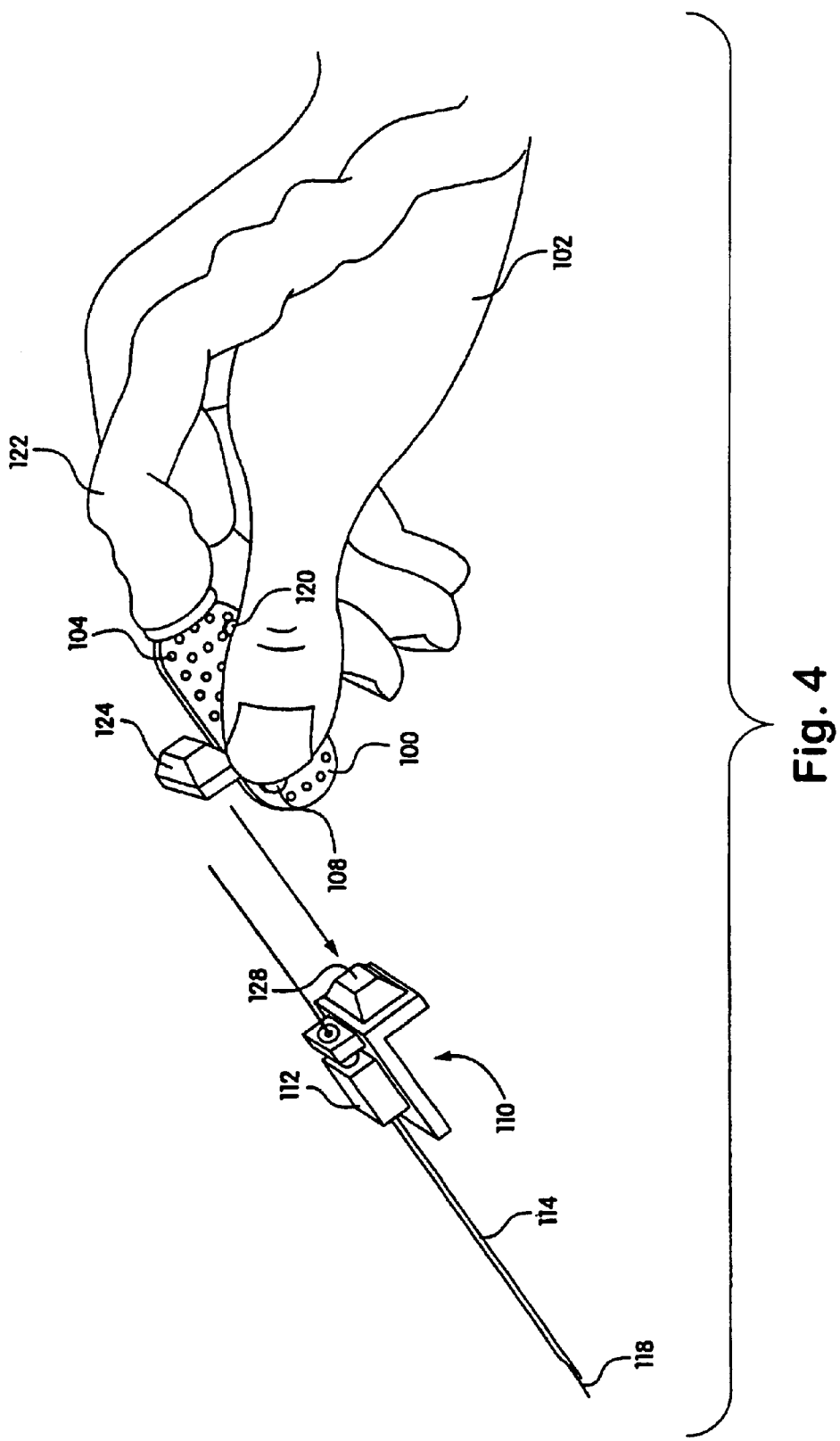
FIG. 4 shows an embodiment of a needle holder assembly held by an operator.

FIG. 4 shows a perspective view of an embodiment of the needle holder assembly 100 as grasped by an operator's hand 102. A grasping surface 104 provides a place where the needle holder assembly 100 can be manipulated by the operator. A textured surface at the grasping surface 104 can indicate the precise location for grasping to optimize control. A push button 108 can be available for releasing the saddle assembly 110 upon which is mounted a needle hub 112, here shown in continuity with a prelocalization needle apparatus 114 through which a j-wire 118 can be placed. An ejector button 120 is available at the proximal edge of the grasping surface 104 to permit the release of the sensor cable 122 connecting the needle holder assembly 100 and the sensors (not shown) in continuity with it to the remaining components of the tracking system (not shown). In the illustrated embodiment, a coupler 124 is shown in continuity with the grasping surface 104. The coupler 124, when coupled to the coupling end 128 of the saddle assembly I 10, allows transmission of information regarding the position of the needle hub 112 and needle apparatus 114 to the remaining components of the tracking system.

Figures 5, 5A:
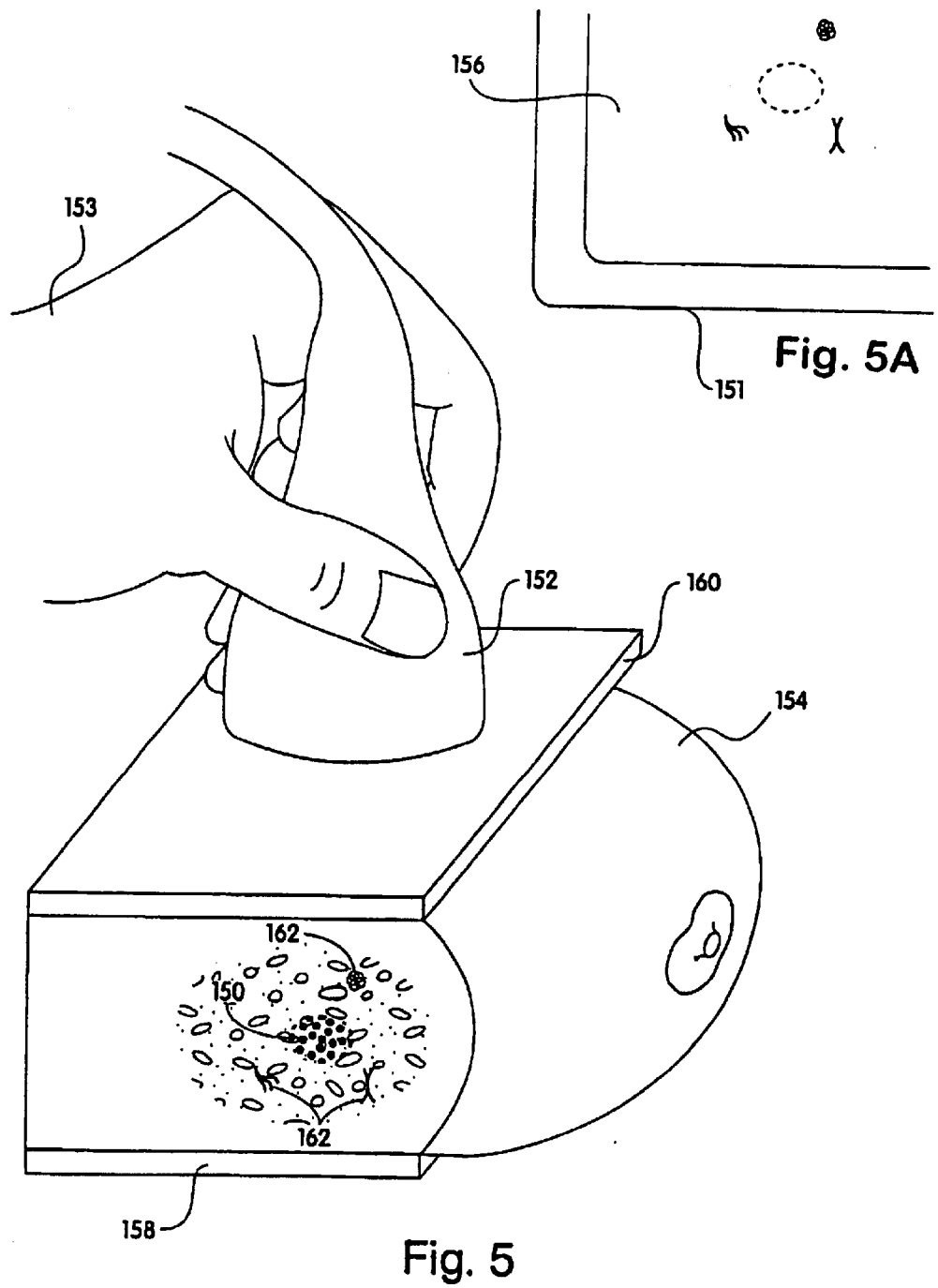
FIGS. 5 and 5A show a schematic perspective view of an operator identifying anatomic landmarks in a compressed breast.

FIGS. 5 and 5A show an embodiment of the systems of the present invention, wherein an operator 153 uses an ultrasound apparatus 152 to identify set of anatomic landmarks 162 in a breast 154, here shown compressed between an upper mammographic plate 160 and a lower mammographic plate 158. In the illustrated embodiment, the ultrasound apparatus 152 is capable of being used through the upper mammographic plate 160. The ultrasound apparatus 152 may also be used to identify a lesion 150. According to the systems and methods of the present invention, however, the lesion 150 need not be visible to the ultrasound apparatus 152. Rather, the position of the lesion 150 can be determined using the systems and methods as previously described. Once the position of the anatomic landmarks 162 has been determined using the ultrasound device 152, the systems and methods of the present invention can determine the relative position of the lesion 150 with respect to the anatomic landmarks 162. Information about this position can be processed and stored to provide a data map 156 allowing the lesion 150 to be localized in a future procedure simply by reference to the anatomic landmarks 162. FIG. 5A shows a schematic of a data map 156 being displayed on a user interface 151. As described previously, a variety of images can be formed to indicate the positional data of the data map 156. A representative illustration of a data map 156 is shown in this figure, but it is understood that alternate types and formats for data display may be readily envisioned by practitioners of ordinary skill in the relevant arts.

Figure 6:
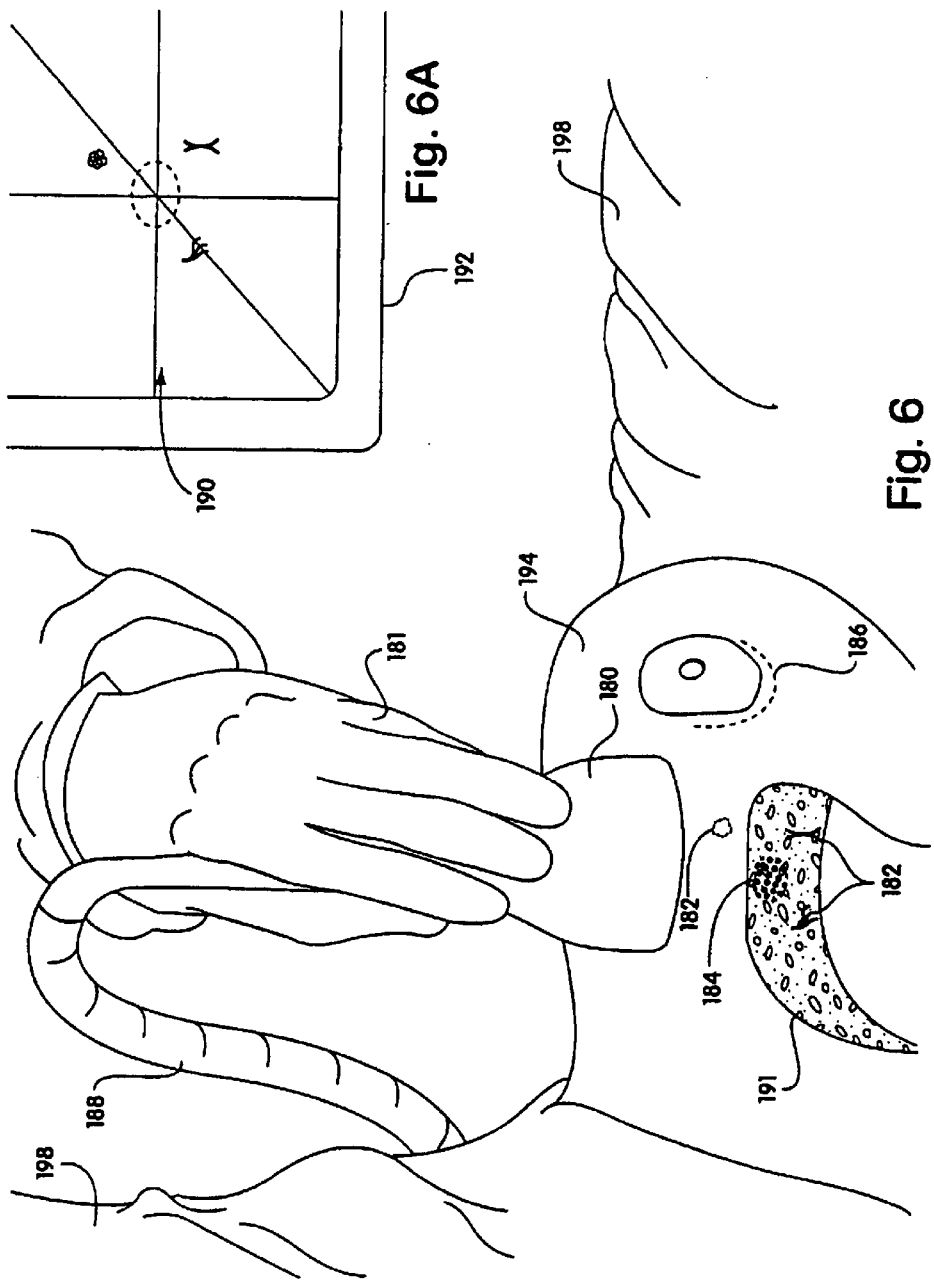

FIGS. 6 and 6A show an embodiment of the systems of the present invention as they may be used in the operating room. In the depicted embodiment, an ultrasound apparatus 180 is employed by an operator 181 to identify a set of anatomic landmarks 182 in a breast 194 of a patient who is shown here covered with surgical drapes 198 undergoing a sterile procedure. In FIG. 6, the ultrasound apparatus 180 may be provided to the operator 181 sterilely, or may be draped sterilely. Similarly, the cable 188 for the ultrasound apparatus 180 may be enclosed in a sterile covering as shown here. The signals obtained from the ultrasound apparatus 180 may then be processed within the systems of the present invention. These systems may refer to a data map (not shown) previously created by ultrasound, as described with reference to FIGS. 5 and 5A, to produce a graphic representation 190 that shows the position of the breast lesion in relation to the landmarks. As previously discussed, the graphic representation 190 of the three-dimensional position of the lesion relative to the landmarks may be produced even though the breast lesion 184 itself is not discernible by the ultrasound apparatus 180. In FIG. 6A the graphic representation 190 is visible on a display monitor 192.

The graphic representation 190 obtained on the free-form unconfined and uncompressed breast 194 in the operating room may further be used to direct a surgical procedure that may be performed at the same time. After it has been captured and displayed, the graphic representation 190 may be used to guide a surgical instrument towards the lesion 184 in real time. In FIG. 6, a periareolar incision 186 has been designed on the surface of the breast 194. After ultrasound has been used to produce a graphic representation 190 of the position of the breast lesion 184 in relation to the anatomic landmarks 182, a surgical instrument (not shown) bearing a tracking system according to the present invention may be directed towards the lesion by reliance upon the graphic representation 190 and any subsequent graphic representation on the display 192 of the position of the surgical instrument relative to the lesion. Systems and methods for directing a surgical instrument towards a lesion have been previously described and have been depicted in certain of the preceding figures. Briefly, in one embodiment, a surgical instrument bearing a tracking system may be introduced sterilely onto the surgical field and it may be dimensionally calibrated so that its position is coordinated with the positional coordinates previously entered into the system via ultrasound relating the position of the anatomic landmarks to the position of the lesion. Once calibrated, the surgical instrument's position may be represented on the display screen by a preselected type of representation. In one embodiment, he position of the surgical instrument may appear on the display screen against a backdrop of the graphic representation 190 previously portrayed. In another embodiment, the graphic representation 190 may be altered or replaced by a different representation that indicates the position of the surgical instrument relative to the lesion. A number of types of representations have been previously described, and others will be readily envisioned by those of ordinary skill in the art. The surgical instrument may be used for any diagnostic or therapeutic purpose. In FIG. 6, the periareolar incision 186 may be used to provide the surgical instrument with access to the breast parenchyma. The extirpation of the lesion 184 may then be guided by the positional guidance that is provided to the surgeon by the representation systems of the present invention. The combination of the tracking system, the representation system and the input from the ultrasound apparatus 180 in delineating the anatomic landmarks 182 according to the systems and methods of the present invention permits a guided biopsy or a wide excision to be performed on a breast lesion 184 in a free-form non-compressed breast 194.

The systems and methods described herein permit the practice of a method for guiding the placement of a surgical instrument into a positional relationship with a lesion. According to a practice of this method, the position of the lesion in three-dimensional space can be determined and correlated with the position of an anatomic landmark. In one practice, the anatomic landmark will comprise a set of structures identified by a diagnostic modality, for example, ultrasound. Ultrasound can provide data regarding the position of an anatomic landmark through which a three dimensional position of the landmark can be determined. These positional data can be processed by the representation system to yield a map of the lesion's location with respect to the anatomic landmark. The biopsy procedure can then take place in a different setting. Intraoperative ultrasound can be used to re-identify the relevant anatomic landmark relative to which the lesion's position has been mapped. The tracking system can guide a surgical instrument towards the lesion by reference to the anatomic landmark the ultrasound identifies, locating the lesion even though there is no direct data produced during the procedure pertaining to the location of the lesion itself. Since the intraoperative ultrasound is being used only to identify the anatomic landmark and not to find the lesion, this method can be used to target a lesion that is itself invisible to ultrasound. An analogous method would be employed to use other diagnostic modalities besides ultrasound that allow for the identification of an anatomic landmark relative to which the lesion can be positioned, even if the diagnostic modality itself cannot locate the lesion but can only identify the anatomic landmark.

In an illustrative embodiment, the placement of the surgical instrument is guided towards a lesion by using ultrasound. In this illustrative embodiment, a lesion of the breast is to be biopsied. The systems and methods of the present invention can be applied similarly to lesions in other locations, however, and should not be confined to the diagnosis and treatment of breast disorders. For example, these systems and methods can be used to biopsy a lesion of the axilla or of the inguinal area, for example a lymph node. For the purposes of this illustration, an approach to a breast lesion will be described according to these systems and methods. In an embodiment of these systems and methods, the location of the lesion in three-dimensional space is identified using a data translation system that produces from a set of two-dimensional coordinates a set of three-dimensional coordinates that correlate with the lesion's position. A positioning system is then used to identify the position of at least one anatomic landmark. The positioning system in this embodiment is an ultrasound system, capable of resolving the shape of small structures within the breast such as ductal structures, vascular structures or lymphatic structures. The shape of a single structure or the architectural array of a plurality of structures comprises an anatomic landmark. The tracking system, according to this embodiment, identifies the positioning of the surgical instrument in space, as previously described. In this embodiment, the representation system can produce a representation indicating the position of the instrument relative to either the landmark or the lesion. The representation can take place in real time. A map that locates the position of the lesion relative to the anatomic landmark can be stored within the representation system so that the instrument can be directed towards the lesion by reference to the position of the instrument with respect to the anatomic landmark. Knowing the coordinates of the lesion with respect to the landmark allows these systems to calculate the position of the surgical instrument with respect to the lesion from data indicating the position of the surgical instrument with respect to the landmark.

While certain of the preceding embodiments have featured the use of mammographic images to provide data points representing the position of a lesion, or the use of ultrasound to provide data points representing the position of anatomic landmarks, it is understood that other modalities may also provide data points that can be used by these systems and methods. As will be appreciated by practitioners of ordinary skill, data points may be derived from any modality capable of providing digital positional information, or any modality whose data output may be converted into digital positional information, for example by scanning. Modalities that may provide such information include, but are not limited to, MRI, CT scan, PET scan, thermoscan, radionuclide scan and conventional X-rays. Other modalities may be identified by skilled practitioners using current technologies or as technologies evolve to provide other mechanisms for obtaining positional data regarding the location of lesions or anatomic landmarks.

Figure 7:
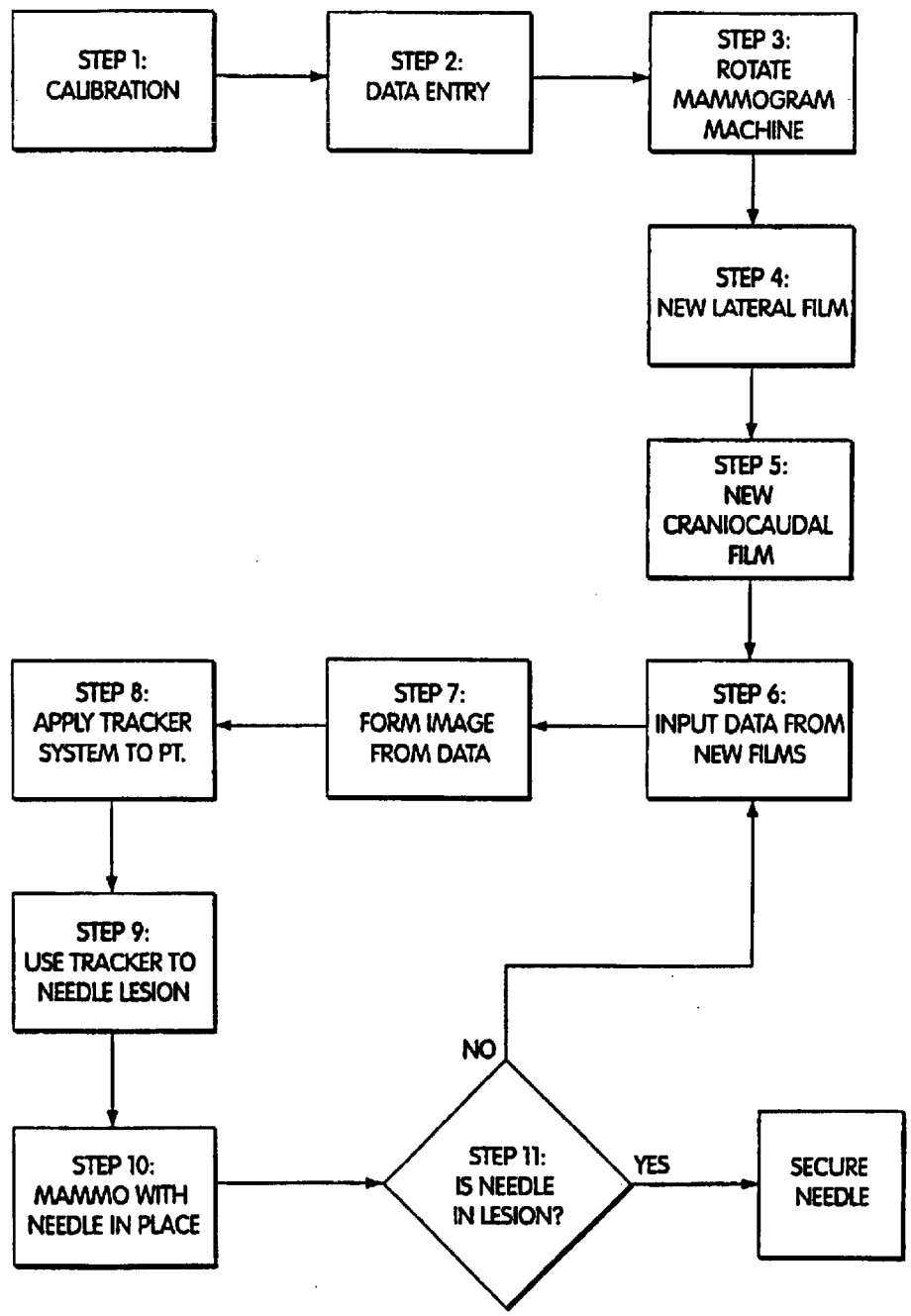
FIG. 7 provides a flow chart summarizing steps of a practice of the present invention.

FIG. 7 shows a flow chart depicting the procedural steps of one practice of a method according to the present invention. In the method illustrated by the flow chart of FIG. 7, a needle can be placed as a needle localization for a subsequent biopsy. Similar procedural steps may be followed according to the method of the present invention to effect the positioning of a surgical instrument relative to a breast lesion. At Step 1, the tracking system is calibrated by the technician. This can be effected by placing the transmitter block and sleeve of the tracking system on a radio-opaque crosshair and activating the calibration system of the tracking system. Calibration is automatically performed through the activation of a software-driven sequence. At Step 2, data from the patient's screening mammograms are entered into the system. The screening lateral film is placed on the screen of the data translation system. The technician can use a stylus that is part of the data translation system to touch the lesion, then the left edge of the breast at the line that has appeared on the screen, followed by the right edge of the breast on the same line. Guidelines and instructions for data input can be produced on the screen by appropriate software. The technician places the screening craniocaudal mammogram film on the screen and uses the stylus in the same manner. At Step 3, the data translation device can interface with the mammography system to produce a set of instructions for reorienting the mammography device. A set of instructions may be provided, comprising an angle and a direction (left or right) for placement of the mammography machine arm for the lateral mammographic film and for the craniocaudal. mammography film. The sum of the two angles in this embodiment is about 90 degrees. The arm of the machine can be rotated to achieve the appropriate angle for the lateral mammogram using this method. At Step 4, a lateral mammogram is taken with the mammogram. device oriented in this position. At Step 5, compression is released and the machine arm can be moved to the next appropriate angle, here determined to be 90 degrees minus the previous angle. A different top plate with a hole and a grid can be used for this film. The patient's breast may again be compressed after being placed on the mammography plate. A craniocaudal film can be taken. Both films may be developed while the breast remains compressed in the craniocaudal position. At Step 6, data can be input into the data translation system from these two films. The lateral film can be placed on the data translation system screen and the stylus can be used to touch the lesion, the left edge of the breast along the line and the right edge of the breast along the same line, all instructions and guidelines being generated by the software within the data translation system. The craniocaudal film data can be input in a similar manner. At Step 7, data thus input can be processed by the representation system to generate an image of the three dimensional position of the lesion. This image can be seen on the user interface of the representation system. At Step 8, the tracker system can be applied to the patient and the surgical instrument. To accomplish this, the technician may apply a sterile pad on the base plate and may apply a tracking sensor to the surgical instrument, for example a needle. The technician may then hand the needle to the radiologist. At Step 9, the radiologist uses the tracking system to target the lesion for approach with the needle. The needle can be calibrated by touching it to the sterile pad. As the radiologist looks at the image with the needle and the lesion on the screen, she can position the needle so that the circle and cross hair on the screen are aligned. She then can enter the breast with the needle. In one embodiment of a representation produced by the representation system, the needle can be oriented towards the lesion by a pattern of concentric circles. A set of concentric circles can appear and disappear on the screen as the lesion is approached. The radiologist can refer to these circles to guide the needle towards the lesions. In one embodiment of the representation, a dotted line may appear to guide the approach to the lesion. When the lesion is reached, the color of the pattern may change as an indicator. The radiologist can then detach the tracking sensor from the needle, leaving the needle in the breast. At Step 10, a confirmatory set of mammograms can be taken with the needle in place. First a craniocaudal film may be taken in the compressed position. Then the compression plates can be released and reapplied at an angle for generating a lateral mammogram. These films can be examined to determine the accuracy of placement. Further steps taken depend upon the decision at Step 11. If placement is satisfactory, the "yes" path at Step 11 can be followed and the needle can be secured in place. If placement is not satisfactory, the "no" path at Step 11 can be followed, and the procedure can return to Step 6, where the films obtained at Step 10 are used to provide the data for the data entry step of Step 6.

EXAMPLES

Example 1

Systems Description in P-Code Format

Background/Setup:

A Tower with the transmitter is affixed to the biopsy plate absolutely. This establishes 0,0,0 relative to the surgical biopsy tool.

There is a Ref Indicator on the tower that is radio-opaque.

The biopsy plate thickness is known and absolute.

Biopsy Plate Indicator locations (A, B, C, . . . . And 1,2, 3 . . . ) relative to Ref Indicator are known and absolute.

Calculation:

Scan the CC Image

Scan the Lat Image

Get Depth from the LAT Image by the following manner
   Present the LAT Image to the User
   Enter Plate Separation(Compression)
   Click on Lesion in the Lat Image
   Detect Left Edge of Breast from Image
   Detect Right Edge of Breast from Image
   Calculate the ratio of Left-Lesion Distance/Lesion-Right Distance
   Multiply Ratio * Plate Separation to get depth Get X,Y Position from CC Image by the following manner
   Present the CC Image to the User
   Either (a)
   Compute Parallax in X and Y from X-Ray specification for each depth
   Click on Lesion in CC Image
   Click on Ref Indicator(known position)
   Calc distance of Lesion X,Y from Ref Indicator X,Y in Pixels from the
   CC Image
   Convert Pixels to MM
   Apply Parallax Adjustment based on depth
   Or (b)
   Enter in Biopsy Plate Indicators Information Use Depth (Depth as calculated above+tool depth+plate thickness) and XY Position as input to Polhemus 3-D 6 Degree of Freedom Magnetic tracker system.

Display and Operation:

Plot current XY position of device relative to Lesion XY and indicate current XY position in concentric target where bulls eye is XY lesion Plot current Depth in Fill Bar where the middle of the fill bar is the depth of the lesion. Above the middle is above the lesion, below the middle is below the lesion.

Display the X, Y and Z(Depth) offsets from the Lesion X,Y and Z(Depth) numerically It is understood that the above figures, examples and descriptions are for illustrative purposes only. Modifications and improvements can be readily envisioned by those of ordinary skill in the relevant arts, and are intended to fall within the scope of the present invention. The foregoing description, therefore, is by way of example only and is not intended to be limiting. Rather, the invention is limited only by the following claims and the equivalents thereto.

We claim:

1. A system for guiding a surgical instrument into a spatial relationship with a lesion, comprising:
    a data translation system for translating a set of data points representative of a position of the lesion in at least two two-dimensional planes into a set of three-dimensional coordinates representative of the position of the lesion in three-dimensional space,
    a tracking system including a sensor positioned on the surgical instrument to generate tracking signals derived from the sensor for identifying the position of the surgical instrument in three dimensional space, and
    a representation system for producing a representation of the position of the surgical instrument and the position of the lesion in three dimensional space relative to each other, as a function of the tracking signals derived from the sensor and the set of three-dimensional coordinates produced by the data translation system, whereby the placement of the surgical instrument into the anatomic relationship with the lesion is guided by reference to the representation produced by the representation system.

2. The system of claim 1, wherein the set of data points is digitally derived from at least one diagnostic test selected from the group consisting of mammography, ultrasound, MRI, CT scan, PET scan, thermal scan, conventional XRay modalities and radionuclide scan.

3. The system of claim 1, wherein the set of data points identifying the position of the lesion is derived from a set of at least two mammograms.

4. The system of claim 1, wherein said representation system produces a data set representing the position of the surgical instrument and the lesion relative to each other in three-dimensional space.

5. The system of claim 1, wherein the representation produced by the representation system comprises at least one visual image.

6. The system of claim 5, wherein the at least one visual image comprises a non representational image graphically representing the position of the surgical instrument and the lesion relative to each other in three-dimensional space.

7. The system of claim 1, wherein the representation produced by the representation system represents a real-time change in the position of the surgical instrument relative to the lesion.

8. The system of claim 1, further comprising an acquisition system for obtaining the set of data points identifying a position of the lesion in the at least two two-dimensional planes.

9. The system of claim 8, wherein the acquisition system comprises a mammography system.

10. The system of claim 1, further comprising an introduction system wherein the introduction system directs the surgical instrument into the positional relationship with the lesion.

11. A system for guiding a surgical instrument into a spatial relationship with a lesion, comprising:
    a data translation system for translating a set of data points representative of the lesion in at least two two-dimensional planes into a set of three-dimensional coordinates representative of the position of the lesion in three-dimensional space,
    a positioning system for identifying the position of the lesion in three-dimensional space relative to a three dimensional position of at least one anatomic landmark,
    a tracking system disposed in relation to the surgical instrument, wherein said tracking system generates tracking signals for identifying the position of the surgical instrument in three dimensional space, and
    a representation system for producing at least one representation relating the position of the surgical instrument in three dimensional space to the position of at least one structure selected from the group consisting of the at least one anatomic landmark and the lesion,
    whereby the placement of the surgical instrument into the anatomic relationship with the lesion is guided by reference to the representation produced by the representation system.

12. The system of claim 11, wherein the three-dimensional position of the at least one anatomic landmark is identified by ultrasound.

13. The system of claim 11, wherein the set of data points is digitally derived from at least one diagnostic test selected from the group consisting of mammography, ultrasound, MRI, CT scan, PET scan, thermal scan, conventional XRay modalities and radionuclide scan.

14. The system of claim 11, wherein the positioning system comprises a device for identifying the three-dimensional position of the at least one anatomic landmark in real time.

15. The system of claim 14 wherein the device for identifying the three-dimensional position of the at least one anatomic landmark in real time comprises an ultrasound device.

16. A system for obtaining a tissue sample from a selected area of a breast, comprising:
    a surgical instrument adapted for obtaining the tissue sample,
    a mammography system for translating two-dimensional data obtained from at least two mammograms into data for identifying a three-dimensional position of the selected area of the breast,
    a tracking system for tracking the three-dimensional position of the surgical instrument relative to the selected area of the breast,
    a positional representation system for producing a representation that represents the three-dimensional position of the surgical instrument relative to the selected area of the breast in real time, and
    an introduction system for directing the surgical instrument in a selected direction relative to the selected area of the breast, said selected direction being determined by reference to the representation produced by the positional representation system, whereby the surgical instrument is directed to the selected area of the breast, therefrom to obtain the tissue sample.

17. The system of claim 16, wherein the mammography system comprises a reference point external to the breast.

18. The system of claim 16, wherein the introduction system is adapted for use by a human operator.

19. A mammography system for orienting a breast to facilitate a biopsy of a breast lesion, comprising
   a mammography device for obtaining mammograms in at least two different planes and capable of obtaining mammograms in a plurality of planes relative to a defined axis of a breast,
   a first set of mammograms, wherein said first set of mammograms identifies a position of the breast lesion within the breast,
   a first set of two-dimensional coordinates that corresponds to the first set of mammograms,
   an adjustment system adapted to generate a set of positional instructions for the mammography device from the first set of mammograms, wherein the set of positional instructions directs the positioning of the mammography device relative to the breast to obtain a second set of mammograms wherein the breast lesion is located centrally on at least one mammogram, and
   a compression system for securing the breast in relation to the mammography system so that the position of the lesion within the breast relative to the mammography system corresponds to the position of the lesion located on the second set of mammograms,
   thereby orienting the breast to facilitate the biopsy of the breast lesion.

20. A method for obtaining a tissue sample from a target area of a breast, comprising:
   identifying the target area on at least two mammograms,
   determining the position of the target area on the at least two mammograms,
   digitizing data correlated with the at least two mammograms that represents the position of the target area,
   determining the position of the target area in three-dimensional space using digitized data correlated with the at least two mammograms,
   creating a first representation from the digitized data indicating the position of the target area in three-dimensional space,
   providing a surgical instrument for obtaining the tissue sample,
   tracking the position of the surgical instrument relative to the target area,
   creating a second representation, wherein the second representation indicates in real time the position of the surgical instrument relative to the position of the target area,
   directing the surgical instrument to the selected area of the breast by referring to the second representation, and
   employing the surgical instrument to obtain a tissue sample from the selected area of the breast.

21. A method for directing a biopsy of a breast lesion, comprising:
   analyzing a set of data correlated with a first set of at least two mammograms to produce a set of correction factors for positioning a mammography device on a breast, whereby said correction factors orient the mammography device so that the breast lesion is centrally located relative to at least one plane for mammogramming the breast,
   positioning the mammography device according to the correction factors,
   securing the breast in the mammography device,
   producing a second set of at least two mammograms based on the position of mammography device as oriented according to the correction factors, and
   using the second set of at least two mammograms to direct the biopsy of the breast lesion.

22. A method for treating a breast abnormality, comprising:
   identifying the breast abnormality on at least two mammograms,
   determining a position of the breast abnormality on at least two mammograms,
   digitizing data correlated with the at least two mammograms that represents the position of the breast abnormality,
   creating from the digitized data a first representation of the position of the breast abnormality,
   providing a surgical instrument for treating the breast abnormality,
   tracking the position of the surgical instrument relative to the breast abnormality,
   creating a second representation, wherein the second representation indicates in real time the position of the surgical instrument relative to the position of the breast abnormality,
   directing the surgical instrument to the breast abnormality by referring to the second representation,
   positioning the surgical instrument in proximity to the breast abnormality, and
   employing the surgical instrument to deliver a treatment to the breast abnormality.

* * * * *